United States Patent [19]

Hoeschel et al.

[11] 4,291,027

[45] Sep. 22, 1981

[54] METHOD FOR TREATING TUMORS WITH ETHYLENEDIAMINE PLATINUM (II) AND 1,2-DIAMINOCYCLOHEXANE-PLATINUM (II) PYROPHOSPHATE COMPLEXES

[75] Inventors: James D. Hoeschel, Oak Ridge, Tenn.; Alan R. Amundsen, Somerville, N.J.

[73] Assignee: Engelhard Minerals & Chemicals Corp., Iselin, N.J.

[21] Appl. No.: 106,439

[22] Filed: Dec. 26, 1979

Related U.S. Application Data

[62] Division of Ser. No. 17,993, Mar. 7, 1979, Pat. No. 4,234,500.

[51] Int. Cl.$^3$ .................. A61K 31/685; A61K 31/66; A61K 31/28
[52] U.S. Cl. .................................... 424/197; 424/204; 424/287
[58] Field of Search .................. 424/199, 287, 204

[56] References Cited

U.S. PATENT DOCUMENTS 4,115,418  9/1978  Gale et al. ..................... 260/429 R
4,140,707  2/1979  Cleare et al. .................. 260/429 R

OTHER PUBLICATIONS

Cleare, Platinum Coordination Complexes in Cancer Chemotherapy Springer-Verlag, N.Y., pp. 24-26, (1974).
Schwartz et al., Cancer Treatment Rep. 61, pp. 519-525, (1977).
Cleare et al., Bioinorganic Chemistry 2, pp. 196-200, (1973).
Leh et al., J. of Pharmaceutical Sciences, 65 (No. 3), pp. 319-320, (1976).

Primary Examiner—Jerome D. Goldberg

[57] ABSTRACT

Ethylenediamine platinum (II) and 1,2-diaminocyclohexane platinum (II) pyrophosphate complexes are prepared by reaction of the appropriate diaquo platinum (II) salt with a pyrophosphate salt. These complexes possess pronounced anti-tumor activity and low toxicity and thus have high therapeutic indices.

5 Claims, 2 Drawing Figures

METHOD FOR TREATING TUMORS WITH ETHYLENEDIAMINE PLATINUM (II) AND 1,2-DIAMINOCYCLOHEXANE-PLATINUM (II) PYROPHOSPHATE COMPLEXES

This is a division of application Ser. No. 17,993 filed Mar. 7, 1979, now U.S. Pat. No. 4,234,500.

This invention is concerned with certain complexes of platinum(II) containing a pyrophosphate moiety and a bidentate amine moiety. More particularly, this invention is concerned with amine platinum(II) pyrophosphate complexes where the amine moiety is an ethylenediamine or a 1,2-diaminocyclohexane moiety. These compounds have the general formula $[\{Pt(A)\}_2P_2O_7]$, where A is either an ethylenediamine or a 1,2-diaminocyclohexane moiety. These complexes are characterized by pronounced activity against in mice combined with low animal toxicity.

BACKGROUND

Figure 1:
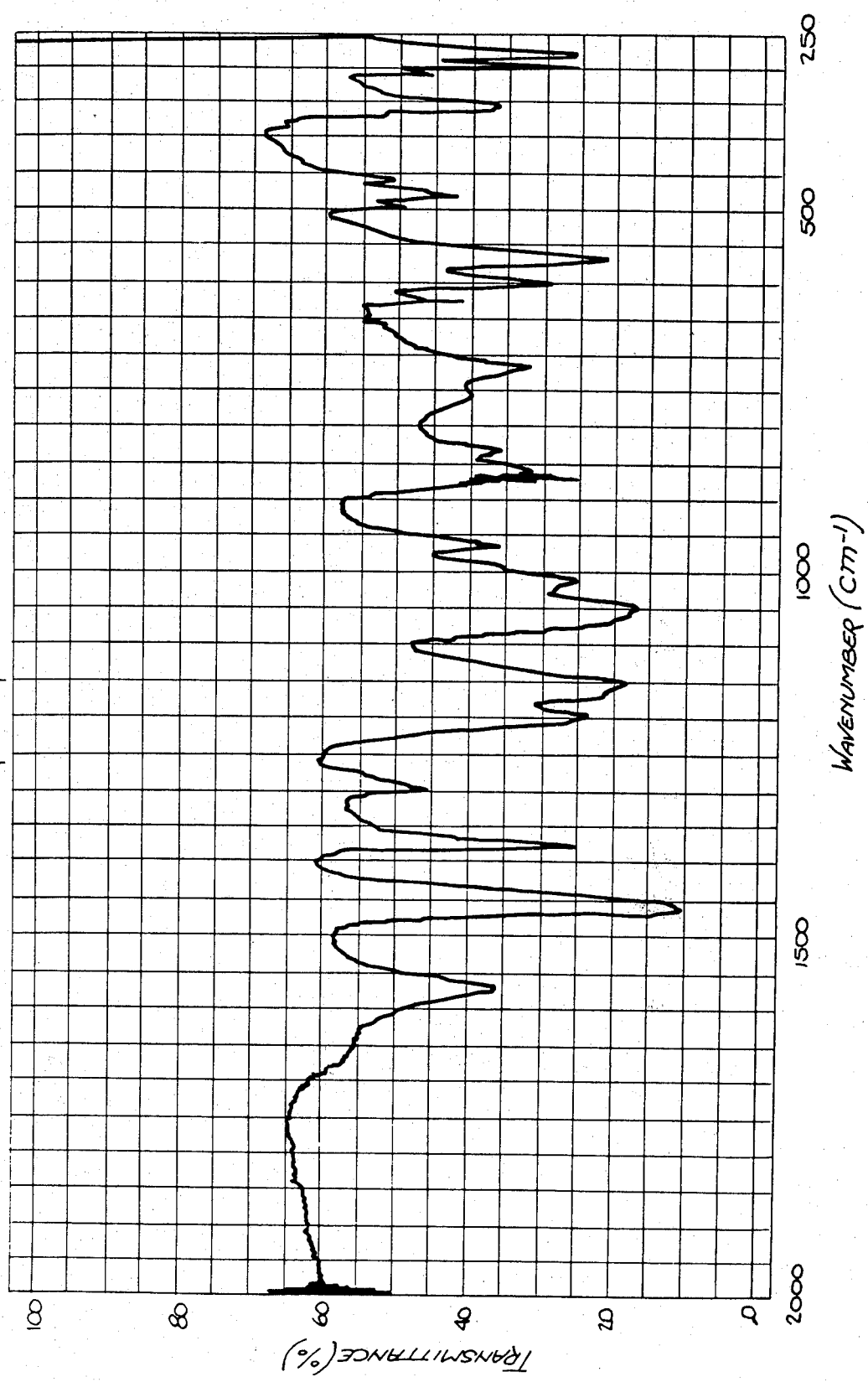
FIG. 1 shows the infrared spectrum of the ethylenediamine platinum(II) pyrophosphate complex of Example 1.

Rosenberg et al reported the discovery that certain platinum coordination compounds are of interest as potential antitumor agents. (Rosenberg et al, "Platinum Compounds: A new Class of Potent Anti-Tumor Agents," Nature, Vol. 222 (Apr. 26. 1969), pp. 385–86). Since then, considerable effort has been expended to evaluate various classes of coordination complexes for similar activity. See, e.g., M. J. Cleare, "Transition Metal Complexes in Cancer Chemotherapy," Coordination Chemistry Reviews, 12 (1974), pp. 349–405. Cis-diammineplatinum pyrophosphate complexes of the empirical formula $\{Pt(NH_3)_2\}_2P_2O_7$ have been reported; however, they have only marginal activity. (Cleare et al, "Studies of the Antitumor Activity of Group VIII Transition Metal Complexes, Part I, Platinum(II) Complexes, Bioinorganic Chemistry, 2, 187–210 (1973) at p. 199.)

A blue, water soluble, orthophosphate complex of 1,2-diaminocyclohexaneplatinum(II) containing 45.85% platinum (Pt) has been reported to show antitumor activity (G. R. Gale et al, "Preparation and Antitumor Evaluation of Water-Soluble Derivatives of Dichloro-1,2-diaminocyclohexane platinum," Cancer Treatment Reports 61, pp. 1519-1525 (1977).

SUMMARY OF THE INVENTION

In accordance with the present invention, there are provided novel ethylenediamine platinum(II) and 1,2-diaminocyclohexane platinum(II) pyrophosphate complexes which, unlike the known pyrophosphate complex, have exhibited pronounced anti-tumor activity in mice. In addition, they have low mammalian toxicity. As a consequence, in addition to their marked activity, the complexes of this invention have a favorable therapeutic index.

The complexes of this invention may be represented by the general formula $[\{Pt(A)\}_2P_2O_7]$. Thus, pyrophosphate comprises a tetravalent moiety which is represented by the formula $P_2O_7^{-4}$.

The remainder of the platinum(II) complexes of this invention comprises a Pt(II)A moiety, wherein A is a bidentate diamine moiety. Thus, A may be represented by the general formula:

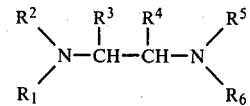

wherein each of $R^1$–$R^6$, when taken separately, is hydrogen or lower alkyl; and $R^3$ and $R^4$, when taken together, form the divalent radical:

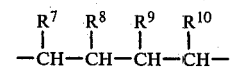

wherein each of $R^7$–$R^{10}$, when taken separately, is hydrogen or lower alkyl, giving a 1,2-diaminocyclohexane with the structure:

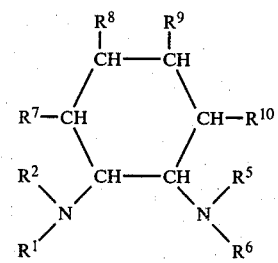

By the term "lower alkyl", as employed herein, is meant a linear or branched chain alkyl group of from 1 to about 6 carbons, and preferably from 1 to about 3 carbons, such as methyl, ethyl and propyl. Preferred diamines where at least five of said $R^1$–$R^6$ are hydrogen, such as ethylenediamine and propylene-1,2-diamine. Also preferred are the diamines where at least three of $R^1$, $R^2$, $R^5$ and $R^6$ are hydrogen, and $R^3$ and $R^4$, when taken together, are replaced by the

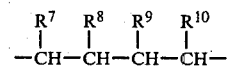

radical wherein, each of $R^7$–$R^{10}$ is hydrogen, such as 1,2-diaminocyclohexane.

The complexes of this invention are prepared by reacting a diaquodiamineplatinum(II) salt with a pyrophosphate salt in an aqueous medium. The diaquodiamineplatinum(II) salt may be represented by the formula:

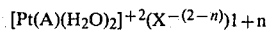

wherein X is an inorganic anion and n is 0 or 1. Suitable anions are those which are stable in acid media and which do not affect pH; they include sulfate, nitrate and perchlorate, although nitrate is preferred. Anions having a greater complexing ability than water or pyrophosphate, such as chloride, iodide and bromide are not suitable.

The diaquo salt is formed by the stoichiometric reaction of the appropriate dichlorodiamineplatinum(II) analogue with a silver salt, preferably silver nitrate, in an aqueous medium at room temperature. The diaquo salt is unstable in solution, but may be converted to stable solid $[Pt(A)(OH)]_2(X)_2$ by reaction with one gram mole of base per gram atom of platinum. This dimeric complex may be reconverted to monomer with acid or used directly in the preparation of phosphate compounds.

The pyrophosphate salts which are employed are water soluble salts, preferably alkali metal pyrophosphate salts such as tetrasodium pyrophosphate.

The pyrophosphate complexes of this invention are prepared by the reaction of equimolar amounts of a diaquoplatinum(II) salt with the general formula $[Pt(A)(H_2O)_2]X_2$ and a pyrophosphate salt, such as tetrasodium pyrophosphate in aqueous media. The reaction proceeds according to the following equation:

$$[\{Pt(A)(H_2O)\}_2]X_2 + P_2O_7^{-4} \rightarrow [Pt(A)_2P_2O_7]$$

Upon the first mixing of the reactants, a white precipitate forms, which, when A is an ethylenediamine moiety, may be converted to the desired yellow end product by one of the following methods: (1) recrystallization of the white solid from boiling water; or (2) briefly boiling the initial reaction mixture with the yellow product separating upon cooling. Addition of nitric acid (less than one gram mole nitric acid per gram atom platinum) to the mixture while it is boiling will increase the yield of the yellow product. When A is a 1,2-diaminocyclohexane moiety, the yellow end product is obtained by drying the while solid in a vacuum desiccator at room temperature for 24 hours.

The complexes of this invention are especially useful in tumor chemotherapy, having been found active against sarcoma 180 ascites, lymphoid leukemia L1210, lymphocitic leukemia P388 and B16 melanoma in mice. The complex is administered intraperitoneally as a slurry with a suspending agent such as Klucel (hydroxypropyl cellulose). The slurry may contain other components, such as physiologically acceptable salts, other medicaments, etc. The dosage level required for anti-tumor activity is not narrowly critical, and indeed it is a feature of the complexes of this invention that, because of their relatively low toxicity, they may be administered over a wide dosage range. In mice, dosages from about 5 to about 30 mg/kg of body weight have been found effective.

The following examples are illustrative. In the examples, the symbol "en" designates the ethylenediamine moiety and the symbol "DAC" designates the 1,2-diaminocyclohexane moiety.

EXAMPLE 1

Synthesis of Ethylenediamine Platinum(II) Pyrophosphate Complex

A 13.4 gram portion of solid $Na_4P_2O_7 \cdot 10H_2O$ was added to 120 ml of a 0.25 M solution of $[Pt(en)(H_2O)_2](NO_3)_2$ so that the pyrophosphate to platinum ratio was about 1. A milky precipitate was produced which dissolved upon heating the mixture to boiling. The addition of 3 ml of 9 M nitric acid immediately precipitated a yellow crystalline solid. Cooling the mixture to about 5° C. and storing it at that temperature for about 6 or 7 hours produced more of the yellow solid. This yellow product was filtered, washed with water and ethanol, and air dried, yielding 4.59 grams (or 44.7% based on Pt analysis) of the above identified complex. The complex appeared to be completely air stable.

Elemental analysis of the complex gave the following results:

Analysis 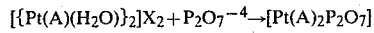 $[\{Pt(C_2H_8N_2)\}_2P_2O_7]$

| | % Pt | % C | % H | % N | % P |
|---|---|---|---|---|---|
| Calculated: | 57.02 | 7.02 | 2.36 | 8.19 | 9.05 |
| Found: | 57.21 | 7.11 | 2.45 | 7.96 | 8.95 |

The infrared spectrum for this complex is attached as FIG. 1. The bands at 1200, 1150, 1050, 1010 and 960 cm$^{-1}$ are assigned to the coordinated pyrophosphate moiety. The band at 1575 cm$^{-1}$ is assigned to $\delta_{NH_2}$. The band at 860 cm$^{-1}$ is assigned to $\rho_{NH_2}$. The band at 560 cm$^{-1}$ is assigned to $\nu_{Pt-N}$. The bands at 450 cm$^{-1}$ and 500 cm$^{-1}$ are assigned to $\nu_{Pt-O}$.

EXAMPLE 2

Synthesis of 1,2-Diaminocyclohexane Platinum(II) Pyrophosphate Complex

A solution made of 5.09 grams $Na_4P_2O_7 \cdot 10H_2O$ dissolved in 40 ml water was slowly added to 200 ml of a 0.057 M solution of $[Pt(DAC)(H_2O)_2](NO_3)_2$. A white precipitate began to form almost immediately upon addition of the pyrophosphate solution. The reaction mixture was stirred overnight, then filtered. The resulting solid filtrate was washed three times with cold water to yield the above-identified complex as an off-white solid that had a very slight green tinge when wet. The complex was air and vacuum-dried, yielding 0.302 grams of yellow complex which was similar in appearance to the complex of Example 1. The yellow complex was not air stable and was reconverted to the white material upon standing in air for 24 hours.

Elemental analysis of the complex gave the following results:

Analysis: $[\{Pt(C_6H_{14}N_2)\}_2P_2O_7]$

| | % Pt | % C | % H | % N | % P |
|---|---|---|---|---|---|
| Calculated: | 49.23 | 18.19 | 3.56 | 7.07 | 7.82 |
| Found: | 52.34 | 17.93 | 3.58 | 6.83 | 8.10 |

Figure 2:
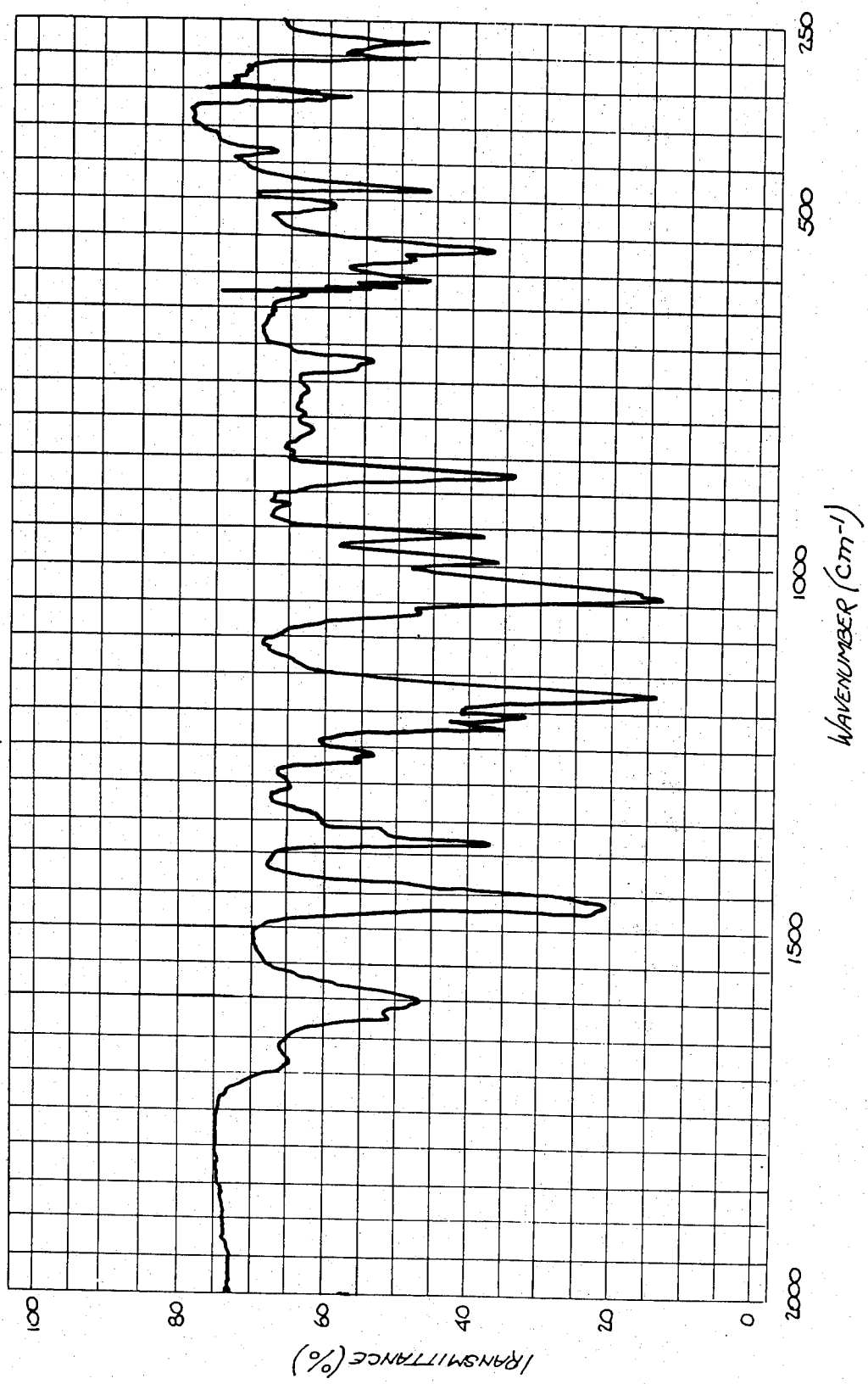
FIG. 2 shows the infrared spectrum of the 1,2-diaminocyclohexane platinum(II) pyrophosphate complex of Example 2.

The infrared spectrum is attached as FIG. 2. The band assignments appear to be the same as those for Example 1.

EXAMPLE 3

Evaluation of Anti-Tumor Activity in the Mouse S180a System

The ethylenediamine platinum(II) pyrophosphate complex of Example 1 and the 1,2-diaminocyclohexane platinum(II) pyrophosphate complex of Example 2 were tested for anti-tumor activity against S180 ascites in female Swiss white mice by the following procedure:

CFW mice, averaging 20 grams, were immediately inspected weighed, and then placed in newly prepared cages (6 mice/cage or 1 set). On day 0 the mice were inoculated with 0.2 ml of a freshly prepared saline suspension (0.15 M NaCl) containing $1 \times 10^7$ tumor cells/ml or a total of $2 \times 10^6$ cells. This inoculum was freshly prepared using "transfer" mice which had been injected with tumor cells the previous week, and was the end-product of a series of steps which involved (1) the removal of the cells from the peritoneal cavity of the sacrificed transfer mouse, (2) alternate centrifugation-washing (2-3 times with cold saline) to remove occasional blood and other undesirable components, and (3) dilution (1:3) of the packed cell volume with saline (the final centriguation being carried out at 1000 rpm for two minutes). A cell count was made (in duplicate) on a 100-fold dilution of this 1:3 suspension (nominally $5 \times 10^7$ cells/ml) by means of a hemacytometer counting chamber and a microscope and in most cases by means of a Coulter Counter. A final dilution to $1 \times 10^7$ cells/ml was made based on the averaged count (normally about 500-600 cells were counted to obtain reliable statistics when the hemacytometer method was employed). On day 1, solutions of the test compounds were prepared and the mice injected with each mouse of a set of six mice being injected with the same test compound at the same dosage level. The doses were based on the average weight of the animals (cage weights).

Also, on day 1 two types of controls were employed: (1)

Normal (1 set): 0.5 ml of the carrier used for the test compound; and (2) Positive Control (1 set): cis-dichlorodiamineplatinum(II), a known anti-tumor agent, used at 7 or 8 mg/kg as a check on the response of the biological test system.

The effectiveness of a compound was measured in terms of the % increase in life span (%ILS) of the test animals relative to the normal controls (calculated from the day of tumor inoculation (day 0). In order to standardize the test data and permit intercomparisons to be made, the day of evaluation was arbitrarily taken as that day corresponding to twice the mean life span (or average day of death) of the controls. This set a practical upper limit of 100% on the %ILS attainable. For purposes of calculation, survivors on the day of evaluation were considered to have died on that day. The %ILS was formulated as:

$$\% ILS = \left( \frac{\text{mean-life span of test mice}}{\text{mean-life span of control mice}} - 1 \right) \times 100\%$$

ILS values in excess of 50% indicate significant anti-tumor activity, while values in excess of 75% indicate high activity.

The water-insoluble complexes of Examples 1 and 2 were tested as slurries in water containing the suspending agent Klucel (0.1 –0.3% Klucel employed).

The data obtained from these tests are summarized in Table I.

TABLE I

Anti-Tumor Screening Data for the Complexes of Examples 1 and 2 obtained on the S180a Tumor System

| Complex of Example # | Dose (mg/kg) | Complex % ILS | 30-day Survivors | 60-day Survivors | Positive Control[a] % ILS | 30-day survivors |
|---|---|---|---|---|---|---|
| 1 | 10 | 99 | 5 | 0 | 63 | 0 |
|  | 20 | 52 | 2 | 0 |  |  |
| 1 | 10 | 62 | 1 | 0 | 60 | 0 |
| 2 | 20 | 62 | 4 | 2 | 63 | 0 |
|  | 40 | −65 | 0 | 0 |  |  |
|  | 80 | −86 | 0 | 0 |  |  |
|  | 160 | −87 | 0 | 0 |  |  |
| 2 | 2.5 | 6 | 0 | 0 | 71 | 1 |
|  | 5 | 30 | 1 | 1 |  |  |
|  | 10 | 78 | 4 | 3 |  |  |
|  | 20 | 73 | 5[b] | 4 |  |  |

[a] Positive control = cis[Pt(NH$_3$)$_2$Cl$_2$] 8 mg/kg in saline.
[b] All tumor free.

Based on the data set forth in Table I, both the complex of Example 1, [{Pt(en)}$_2$P$_2$O$_7$], and the complex of Example 2, [{Pt(DAC)}$_2$P$_2$O$_7$] appeared to be effective against the S180a tumor screening system. The complex of Example 1 was active at doses of 10 and 20 mg/kg; the toxic dose was not reached. The complex of Example 2 was also active at doses of 10 and 20 mg/kg; it appeared toxic at doses of 40 mg/kg and greater.

EXAMPLE 4

Evaluation of Anti-Tumor Activity in the L1210, P388 and B16 Tumor Systems

The complex of Example 1 was also screened for activity against mouse lymphoid leukemia L210, mouse lyphocytic leukemia P388 and mouse melanoma B16. The complex of Example 2 was screened against mouse lymphoid leukemia L1210. In these tests, the mean survival time of the treated mice as compared with that of the control mice (T/C) was determined. The T/C* was calculated as follows:

$$T/C = \left( \frac{\text{mean life span (test)}}{\text{mean life span (control)}} \right) \times 100$$

T/C values of 125 or more represent significant anti-tumor activity.

*T/C is related to %ILS by the relationship T/C−100 = %ILS

The results of these tests are summarized in Table II.

TABLE II

Anti-Tumor Screening Data Results from the B16, L1210 and P388 Tumor Systems

| Complex[c] of Example # | Tumor System | Dose Schedule | Dose Range (mg/kg) | Highest T/C (dose mg/kg) |
|---|---|---|---|---|
| 1 | B16 | a | 0.78–12.5 | 149(6.25) |
|  | B16 | a | 2.66–9.00 | 144(4.00) |
|  | L1210 | b | 1.56–25.0 | 125(12.5) |
|  | L1210 | b | 0.75–24.0 | 127(6.00) |
|  | P388 | a | 0.78–12.5 | 220(6.25) |
|  | P388 | a | 0.78–12.5 | 171(3.13) |
| 2 | L1210 | b | 12.5–200 | 190(12.5) |
|  | L1210 | b | 1.56–50.0 | 140(6.25) | a 9 Daily doses on Days 1–9.
b 3 doses on Days 1, 5, 9.
[c] The carrier for all samples was saline with Tween-80 used as a suspending agent.

Based on the data set forth in Table II, it appears that the complex of Example 1 was reproducibly active against all three of the tumor systems that it was tested against. The complex of Example 2 appeared to show excellent activity against the L1210 tumor system.

What is claimed is:

1. A method for treating malignant sarcoma 180 ascites, lymphoid leukemia L1210, lymphocytic leukemia P388 or B16 melanoma tumors in a mammal afflicted therewith which comprises administering to said mammal an effective amount of an amine platinum(II) pyrophosphate complex useful for treating said tumors, said complex having a structure of the formula:

[{Pt(A)}$_2$P$_2$O$_7$]

wherein A is a diamine of the formula: NR$^1$R$^2$—CHR$^3$—CHR$^4$NR$^5$R$^6$ in which R$^1$-R$^6$, taken separately, are selected from hydrogen or lower alkyl and R$^3$ and R$^4$, taken together, represent the divalent radical: —CHR$^7$—CHR$^8$—CHR$^9$—CHR$^{10}$— wherein R$^7$-R$^{10}$ are selected from the group consisting of hydrogen and lower alkyl.

2. The method according to claim 1 wherein $R^1$–$R^6$ taken separately represent hydrogen or lower alkyl.

3. The method according to claim 1 wherein each of $R^1$–$R^6$ is hydrogen.

4. The method according to claim 1 wherein $R^1$, $R^2$, $R^5$ and $R^6$ are selected from hydrogen or lower alkyl and $R^3$ and $R^4$, taken together, represent the divalent radical: —$CHR^7$—$CHR^8$—$CHR^9$—$CHR^{10}$— wherein $R^7$–$R^{10}$ are selected from the group consisting of hydrogen and lower alkyl.

5. The method according to claim 4 wherein $R^1$, $R^2$, $R^5$ and $R^6$ are hydrogen and $R^3$ and $R^4$, taken together, represent the divalent radical: —$CH_2$—$CH_2$—$CH_2$—$CH_2$—.

* * * * *